United States Patent [19]

Lui et al.

[11] Patent Number: 5,420,364
[45] Date of Patent: May 30, 1995

[54] PROCESS FOR THE PREPARATION OF HALOGENATED AROMATIC COMPOUNDS

[75] Inventors: Norbert Lui, Köln; Albrecht Marhold, Leverkusen, both of Germany

[73] Assignee: Bayer Aktiengesellschaft, Leverkusen, Germany

[21] Appl. No.: 86,697

[22] Filed: Jul. 2, 1993

[30] Foreign Application Priority Data

Jul. 9, 1992 [DE] Germany .................... 42 22 517.5

[51] Int. Cl.⁶ .................. C07C 17/361; C07C 25/02; C07C 25/125; C07C 25/13
[52] U.S. Cl. ..................... 570/142; 568/314; 568/634; 568/656; 570/201
[58] Field of Search .............. 570/142, 201; 568/314, 568/634, 656

[56] References Cited

U.S. PATENT DOCUMENTS

| | | | |
|---|---|---|---|
| 3,087,974 | 4/1963 | Hauptschein et al. | 570/151 |
| 3,283,018 | 11/1966 | Christe et al. | |
| 3,787,331 | 1/1974 | Groppelli et al. | 570/163 |
| 3,793,229 | 2/1974 | Groppelli et al. | 570/163 |
| 4,714,785 | 12/1987 | Manner | 570/201 |
| 4,745,235 | 5/1988 | Ashton et al. | 570/142 |
| 5,026,930 | 6/1991 | Manzer et al. | 570/168 |
| 5,051,537 | 9/1991 | Manzer | 570/168 |

FOREIGN PATENT DOCUMENTS

| | | | |
|---|---|---|---|
| 733990 | 5/1966 | Canada | 570/142 |
| 0118241 | 9/1984 | European Pat. Off. | |
| 0427603 | 5/1990 | European Pat. Off. | |

*Primary Examiner*—Joseph E. Evans
*Attorney, Agent, or Firm*—William C. Gerstenzang; Sprung Horn Kramer & Woods

[57] ABSTRACT

Halogenated aromatic compounds are prepared by passing esters of halogenoformic acid at temperatures in the range 150° to 600° C. and pressures from 0.1 to 3 bar over a catalyst containing chromium, magnesium, iron, silicon and/or aluminium, wherein if Al₂O₃ catalysts are used these have been activated with hydrogen halide.

8 Claims, No Drawings

PROCESS FOR THE PREPARATION OF HALOGENATED AROMATIC COMPOUNDS

The present invention relates to a process for the preparation of halogenated aromatic compounds by catalytic decarboxylation of aromatic esters of halogenoformic acid in the gas phase.

It is known, that in the chlorination of m-dialkylbenzenes, isomeric mixtures are obtained which can only be separated with difficulty and only contain the respective 2,6-dialkylchlorobenzene as minor components (see J.Org. Chem. 55, 5260–5269 (1990)).

2,6-Dialkylfluorobenzene can be prepared more selectively if a tertiary butyl group is first introduced into m-dialkylbenzene in the m position to the two alkyl groups, followed by nitration, reduction, diazotisation, boiling in the presence of fluoride ions and then eliminating the tertiary butyl group (see J. Chem. Soc. Perkin Trans. I 1987, 1). The multiple-stage procedure is a disadvantage.

Another synthesis method for 2,6-dialkylhalogenobenzenes starts from 2,3-dimethylbutadiene, which is reacted with dichlorocarbene, subjected to a rearrangement, dechlorinated using triphenyltin halide and again reacted with dichlorocarbene (see Synthesis, Volume 6–7, Pages 647 to 649). The 2,3-dimethylbutadiene required in this case is difficult to synthesise and thus expensive. The procedure is also highly complex in this case and thus of interest as a laboratory method at most.

Aliphatic esters of fluoroformic and chloroformic acid can be thermally reacted in the presence of Lewis acids to give the corresponding fluoroalkanes and chloroalkanes (see German Offenlegungsschrift 2 931 777, U.S. Pat. No. 4,814,524 and German Patent Specification 857 350).

Aromatic esters of fluoroformic acid can be thermally reacted in the presence of aluminium oxide or noble metal-containing aluminium oxide to give fluorinated aromatic compounds (see EP-A 118 241). The yields achievable in these cases are not satisfactory. Moreover, with the use of chloroformic esters, a large excess of hydrogen fluoride must be used in order to obtain fluorinated aromatic compounds (see EP-A 427 603).

A process has now been found for the preparation of halogenated aromatic compounds of the formula (I)

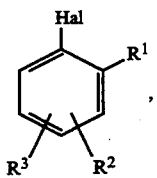

in which
Hal represents fluorine or chlorine,
$R^1$ represents $C_1$-$C_6$-alkyl,
$R^2$ represents hydrogen or $C_2$-$C_6$-alkyl,
$R^3$ represents hydrogen, $C_1$-$C_6$-alkyl, CO—$C_1$-$C_6$-alkyl, fluorine, chlorine or $C_1$-$C_6$-alkoxy and
$R^1$ and $R^2$ together can alternatively form a —CH=CH—CH=CH—bridge,
which is characterised in that a halogenoformic ester of the formula (II)

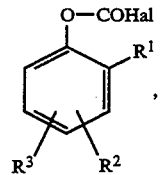

in which the symbols used have the meaning given at formula (I),
is passed at temperatures in the range 150° to 600° C. and pressures from 0.01 to 3 bar over a catalyst containing chromium, magnesium, iron, silicon and/or aluminium, wherein if $Al_2O_3$ catalysts are used these have been activated with hydrogen halide.

In the formulae (I) and (II), preferably,
Hal represents chlorine,
$R^1$ represents methyl, ethyl or i-propyl,
$R^2$ represents hydrogen, methyl, ethyl or i-propyl, or alternatively $R^1$ and $R^2$ together represent a —CH=CH—CH=CH— bridge and
$R^3$ represents hydrogen, methyl, ethyl, i-propyl, $COCH_3$, $COC_2H_5$, fluorine, chlorine, methoxy, ethoxy or i-propoxy.

The radicals $R^2$ and $R^3$ are preferably in ortho- or meta-positions to $R^1$.

Preferred reaction temperatures are in the range 200° to 500° C., preferred pressures in the range 0.1 to 2 bar. The pressure and temperature conditions are always selected such that the compound of the formula (II) occurs in the gas phase immediately prior to the reaction at the catalyst.

The catalysts to be used according to the invention can, for example, be those which contain chromium, magnesium, iron, silicon and/or aluminium in the oxide and/or halide form, $Al_2O_3$ catalysts always being those which have been activated with hydrogen halide. Catalyst constituents can, for example, be: chromium(III) chloride, magnesium oxide, magnesium fluoride, aluminium silicate, silicon dioxide and iron chloride, each of which can be used alone or in any desired mixtures with each other. Iron can also be used in the elemental form as a catalyst, for example in the form of metallic iron, steel, or stainless steel. The catalyst is preferably present in particulate form, for example in particles having a mean diameter of 0.3 to 5 mm.

The catalyst is preferably aluminium oxide which has been activated with hydrogen halide. Such catalysts can, for example, be prepared starting from particulate γ-$Al_2O_3$, which is activated by passing over gaseous hydrogen fluoride or gaseous hydrogen chloride. The passing over of the halides can, for example, be carried out at temperatures between 200° and 500° C. Based on 100 ml of aluminium oxide, for example, 1 to 100 g/h of hydrogen halide can be used for a period of 0.1 to 8 hours. It is advantageous, prior to passing over the hydrogen halide, to dry the aluminium oxide, for example by passing over nitrogen at elevated temperatures.

The compound of the formula (II) can be passed over the catalyst alone or in a mixture with inert gases, for example nitrogen. Per hour, based on 100 g of catalyst, for example, 5 to 100 g of a compound of the formula (II) can be passed over the catalyst.

The hot gas mixture present after passing the compound of the formula (II) over the catalyst can, for example, be worked up by cooling it, for example condensing the portions of the gas mixture condensable at 50° C. or below and isolating from the condensate, for example, by distillation, the compound prepared of the formula (I).

With the aid of the process according to the invention, aromatic esters of halogenoformic acid can be advantageously thermically/catalytically decomposed to give the corresponding halogenated aromatic compounds. In this case, fluorinated and chlorinated aromatic compounds can be obtained selectively without the formation of further isomers. Finally, fluorinated aromatic compounds can be prepared in the absence of hydrogen fluoride.

The halogenated aromatic compounds of the formula (I) which can be synthesised in the manner according to the invention are required as intermediates for the preparation of crop protection agents (see German Patent Application P 4 128 132.2).

EXAMPLES

Example 1 a) Preparation of a Catalyst

In a 35 cm long quartz tube (diameter 25 mm) having an electrical heating coil, 300 ml of $\gamma$-Al$_2$O$_3$ were dried in a nitrogen stream at 450° C. for 48 hours and then anhydrous hydrogen chloride was passed through for 16 hours at a rate of 60 g/h.

b) Reaction of 2,6-Dimethylphenyl Chloroformate 30 g of 2,6-dimethylphenyl chloroformate were passed per hour via a pre-evaporator, comprising a 20 cm long quartz tube (diameter 25 mm), packed with quartz pieces and heated to 280° C., into the quartz tube described under (a), which contained the activated catalyst as described under (a). The reaction temperature was 230° C. At the same time, 24 l/h of nitrogen were passed through the reaction tube. The gases leaving the reaction tube were condensed in a condenser at 20° C. 2-Chloro-1,3-dimethylbenzene formed over a 16 hour period of continuous operation at a selectivity of greater than 95% and at a yield of 85%.

Example 2

The process was carried out as in Example 1, but 20 g of 2,3-dimethylphenyl chloroformate were used per hour. 2,3-Dimethylchlorobenzene was formed at a selectivity of greater than 90%. The condensate collected in the condenser was washed using 5% strength by weight of aqueous sodium hydroxide solution and distilled in vacuo. 2,3-Dimethylchlorobenzene was thus obtained having a boiling point of 187° C. at 1030 mbar at a yield of 54%.

Example 3

The process was carried out as in Example 1, but 20 g of 2,4,6-trimethylphenyl chloroformate were introduced. After condensation of the reaction gas, washing using water and distillation in vacuo, 2,4,6-trimethylchlorobenzene was obtained at a yield of 74% and having a boiling point of 120° C. at 72 mbar.

Example 4

The procedure was carried out as in Example 1, but 20 g of 2,4-dimethylphenyl chloroformate were introduced. The reaction gases were condensed in a condenser, washed using water and distilled in vacuo. 2,4-Dimethylchlorobenzene was obtained at a yield of 31% which had a boiling point of 186° C. at atmospheric pressure.

Example 5

The process was carried out as in Example 1, but 20 g of 1-naphthalenyl chloroformate were introduced. This was 40% converted and 1-chloronaphthalene was detected in the reaction gas in a yield of 34% of theory.

Example 6 a) Preparation of an Al$_2$O$_3$ catalyst activated with hydrogen fluoride 100 g per hour of anhydrous hydrogen fluoride were passed through a nickel tube in which was placed 400 ml of $\gamma$-Al$_2$O$_3$, while the temperature was increased from 250° C. initially to 450° C. at a rate of 20° C. per hour.

b) Decarboxylation of 2,6-dimethylphenyl fluoroformate

In a pre-evaporator as described in Example 1, 10 g of 2,6-dimethylphenyl fluoroformate were evaporated per hour at 360° C. and fed to a quartz reactor (35 cm long, diameter 25 mm) which was packed with the catalyst activated as described under (a) and operated at 350° C. The gases leaving the reactor were condensed in a condenser at $-20$° C. 2,6-Dimethylfluorobenzene had formed in a yield of 80% and at a selectivity of greater than 90%.

Comparison Example 1

150 g of $\gamma$-Al$_2$O$_3$ were dried in a quartz tube (35 cm long, diameter 25 mm) in a nitrogen stream for 36 h at 200° C. 20 g/h of 2,6-dimethylphenyl chloroformate were then passed through the quartz tube at 200° C., the reaction gases were condensed at $-20$° C. and analysed by gas chromatography. In the first two hours of operation, the conversion rate was 100%, then it decreased to 95%, at the same time dimethylphenol was formed up to a proportion of 20% (based on chloroformate).

Comparison Example 2

The process was carried out as in Example 1, but a $\gamma$-Al$_2$O$_3$ was used which contained 30 g/l of iron(III) chloride. The results deviated only slightly from those of Comparison example 1.

Example 7

A CrCl$_3$-MgO catalyst, which contained 17% by weight of CrCl$_3$ and 76% by weight of MgO and had a particle size of 5 mm, was dried for 16 hours in a nitrogen stream at 300° C. 110 ml of the dried catalyst was packed into a stainless steel tube (700 mm long, 14 mm diameter) and were impinged with 10 g per hour of 2,6-dimethylphenyl chloroformate at a temperature of 330° C. The gases leaving the tube were condensed at 0° C. in a condenser and analysed by gas chromatography. 69% of 2,6-dimethyl-chlorobenzene, 21% of 2,6-dimethylphenol, 3% of m-xylene and 7% of unknown by-products were obtained.

Example 8

Particulate magnesium fluoride having a mean diameter of 2 to 3 mm was dried for 3 hours at 300° C. in a nitrogen stream. 150 ml of the magnesium fluoride thus dried were packed into a stainless steel tube (as in Example 7) and impinged with 10 g per hour of 2,6-dimethylphenyl chloroformate at 500° C. The gases leaving the tube were condensed in a condenser at 0° C. and analysed by gas chromatography. The products obtained were: 51% of 2,6-dimethylchlorobenzene, 34% of 2,6-dimethylphenol, 7% of m-xylene and 8% of unknown by-products.

Example 9

150 ml of stainless steel packings (diameter 4 mm) were packed into a reaction tube (see Example 7) and impinged with 20 g per hour of 2,6-dimethylphenyl chloroformate at 530° to 550° C. The reaction gases were condensed in a condenser at 0° C. and analysed by gas chromatography. The products obtained were: 19% of 2,6-dimethylchlorobenzene, 3% of 2,6-dimethylphenol, 3% of 2,6-dimethylphenol, 3% of m-xylene and 5% of unknown by-products.

Example 10

Al$_2$SiO$_5$ (Type PY 700). was dried for 16 hours at 250° C. in a nitrogen stream. 140 ml of the dried product were packed into a reaction tube (see Example 7) and impinged with 20 g per hour of dimethylphenyl chloroformate. The gases leaving the tube were condensed at 0° C. and analysed by gas chromatography. The products obtained were: 72% of 2,6-dimethylchlorobenzene, 5% of 2,6-dimethylphenol, 4% of m-xylene and 16% of unknown by-products.

Example 11

SiO$_2$ (Type AF 125) was dried for 16 hours in a nitrogen stream at 250° C. 140 ml of the dried product were then packed into a reaction tube (see Example 7) and impinged with 20 g per hour of 2,6-dimethylphenyl chloroformate at 370° C. The gases leaving the tube were condensed at 0° C. in a condenser and analysed by gas chromatography. The conversion rate was 40%.

Example 12

5 g of FeCl$_3$ were dissolved at room temperature in anhydrous ethanol, mixed with 150 ml of SiO$_2$ (Type AF 125) and dried in vacuo. The mixture was then heated through for a further 16 hours in the nitrogen stream at 200° C. 2,6-Dimethylphenyl chloroformate was reacted on this catalyst in the procedure described in detail in Example 7. The conversion rate was 8%.

What is claimed is:

1. A process for the preparation of halogenated aromatic compounds of the formula (I)

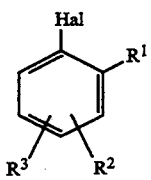

(I)

in which
Hal represents fluorine or chlorine, $R^1$ represents $C_1$-$C_6$-alkyl,
$R^2$ represents hydrogen or $C_1$-$C_6$-alkyl,
$R^3$ represents hydrogen, $C_1$-$C_6$-alkyl, CO—$C_1$-$C_6$-alkyl, fluorine, chlorine or $C_1$-$C_6$-alkoxy and
$R^1$ and $R^2$ together can alternatively form a —CH=CH—CH=CH— bridge, in which a halogenoformic ester of the formula (II)

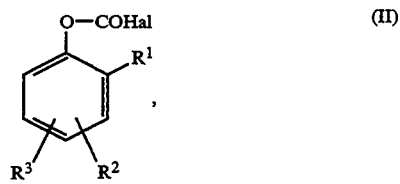

(II)

in which the symbols used have the meaning given at formula (I), is passed, either alone or in a mixture with inert gases, at temperatures in the range 150° to 600° C. and pressures from 0.01 to 3 bar over a catalyst consisting essentially of a member of the group consisting of chromium (III) chloride, magnesium oxide, magnesium fluoride, aluminium silicate, aluminium oxide which has been activated with hydrogen halide, mixtures thereof, and iron in elemental form or in the form of steel or stainless steel, and wherein the pressure and temperature conditions selected are such that said compound of formula II is in the gas phase immediately prior to contacting the catalyst.

2. The process of claim 1, in which in the formulae (I) and (II),
Hal represents chlorine,
$R^1$ represents methyl, ethyl or i-propyl,
$R^2$ represents hydrogen, methyl, ethyl or i-propyl, or $R^1$ and $R^2$ together represent a —CH=CH—CH=CH— bridge and
$R^3$ represents hydrogen, methyl, ethyl, i-propyl, COCH$_3$, COC$_2$H$_5$, fluorine, chlorine, methoxy, ethoxy or i-propoxy.

3. The process of claim 1, in which in the formulae (I) and (II), $R^2$ and $R^3$ are in ortho- or meta-positions to $R^1$.

4. The process of claim 1, in which the reaction temperatures are in the range 200° to 500° C. and the pressures in the range from 0.1 to 2 bar.

5. The process of claim 1, in which the catalyst is aluminium oxide which has been prepared from particulate γ-Al$_2$O$_3$ which was activated by passing over gaseous hydrogen fluoride or gaseous hydrogen chloride.

6. The process of claim 1, in which the compound of the formula (II) is passed over the catalyst alone.

7. The process of claim 1, in which, based on 100 g of catalyst, 5 to 100 g of a compound of the formula (II) are hourly passed over the catalyst.

8. The process of claim 1, in which the hot gas mixture present after gases have been passed over the catalyst is worked up by cooling it, condensing the condensable portions of the gas mixture and isolating from the condensate the compound prepared of the formula (I).

* * * * *

UNITED STATES PATENT AND TRADEMARK OFFICE
CERTIFICATE OF CORRECTION

PATENT NO. : 5,420,364
DATED : May 30, 1995
INVENTOR(S) : Lui, et al.

It is certified that error appears in the above-indentified patent and that said Letters Patent is hereby corrected as shown below:

Col. 6, line 4   Delete " C6 " and substitute -- $C_6$ --

Signed and Sealed this

Thirty-first Day of October 1995

Attest:

BRUCE LEHMAN

Attesting Officer        Commissioner of Patents and Trademarks